US010016356B2

(12) United States Patent
Abdul-Malak et al.

(10) Patent No.: US 10,016,356 B2
(45) Date of Patent: Jul. 10, 2018

(54) SEBUM SECRETION INHIBITORY AGENT

(75) Inventors: Nabil Abdul-Malak, Caluire (FR); Corinne Reymermier, Charly (FR)

(73) Assignee: BASF Beauty Care Solutions France S.A.S., Lyons (FR)

( * ) Notice: Subject to any disclaimer, the term of this patent is extended or adjusted under 35 U.S.C. 154(b) by 0 days.

(21) Appl. No.: 12/623,589

(22) Filed: Nov. 23, 2009

(65) Prior Publication Data
US 2010/0143512 A1 Jun. 10, 2010

Related U.S. Application Data

(60) Provisional application No. 61/121,917, filed on Dec. 12, 2008.

(30) Foreign Application Priority Data

Dec. 1, 2008 (FR) ...................................... 08 58183

(51) Int. Cl.
*A61K 8/97* (2017.01)
*A61Q 19/00* (2006.01)

(52) U.S. Cl.
CPC .............. *A61K 8/97* (2013.01); *A61Q 19/008* (2013.01)

(58) Field of Classification Search
None
See application file for complete search history.

(56) References Cited

U.S. PATENT DOCUMENTS

| | | | |
|---|---|---|---|
| 5,925,679 A * | 7/1999 | Mather et al. | ................ 514/574 |
| 6,403,110 B1 | 6/2002 | Siddiqui et al. | |
| 2004/0180033 A1 | 9/2004 | Msika | |
| 2004/0253220 A1 | 12/2004 | Perrier et al. | |
| 2007/0184012 A1 | 8/2007 | Perrier et al. | |
| 2010/0040710 A1 | 2/2010 | Perrier et al. | |
| 2011/0244063 A1 | 10/2011 | Abdul-Malak et al. | |

FOREIGN PATENT DOCUMENTS

| | | |
|---|---|---|
| EP | 1119344 A1 | 8/2001 |
| FR | 0654316 A | 4/1929 |
| FR | 2855968 A1 | 12/2004 |
| FR | 2863893 A1 | 6/2005 |
| FR | 2893252 A1 | 5/2007 |
| JP | 3007234 A | 1/1991 |
| JP | 11310528 A | 11/1999 |
| JP | 2000095663 A * | 4/2000 |
| JP | 2001031528 A | 2/2001 |
| JP | 2002241295 A * | 8/2002 |
| JP | 2003026594 A | 1/2003 |
| JP | 2006/306816 A | 11/2006 |
| WO | WO-99/59538 A1 | 11/1999 |
| WO | WO-00/19974 | 4/2000 |
| WO | WO-2005/087245 A1 | 9/2005 |

OTHER PUBLICATIONS

Howard, D. "what is Acne". Retrieved from the Internet on: Nov. 12, 2016. Retrieved from: <URL: http://www.dermalinstitute.com/ir/assets/articles/19_pdf_53a206815d34c_What%20ls%20Acne.pdf>.*
"Kioskea.net". Acne. Internet Publication Date: Nov. 2014 [Retrieved from the internet on: Jun. 6, 2017]. Retrieved from: <URL: http://static.ccm2.net/health.ccm.net/faq/pdf/acne-29-mnoju1.pdf?new>.*
Gupta, RC. "Cradle Cap: Infantile Seborrhieic Dermatitis". Internet Publication Date: Aug. 2014. [Retrieved from the Internet on: Jun. 6, 2017]. Retrieved from: <URL: http://kidshealth.org/en/parents/cradle-cap.html#>.*
Johnson et al. "Treatment of Seborrheic Dermatits".Am Fam Physician. May 1, 2000;61(9): 6 pages.*
Preliminary Search Report, dated Jun. 17, 2009.
XP-002532460, Database WPI Week 200322, Thomson Scientific, London, GB; AN 2003-224046 & JP 2002 241295 A (Nonogawa Shoji KK) Aug. 28, 2002 (Aug. 28, 2002), abstract.
XP-002532462, Database WPI Week 200031, Thomson Scientific, London, GB; AN 2000-353406 & JP 2000 095663 A (Kose KK) Apr. 4, 2000 (Apr. 4, 2000), abstract.
Chen, C.-P., et al., "Development of Natural Crude Drug Resources from Taiwan (VI)—In vitro Studies of the Inhibitory Effect on 12 Microorganisms", Shoyakugaku Zasshi, 1987, vol. 41, No. 3, pp. 215-225.
Lamaison, J. L., et al., "Teneurs en Acide Rosmarinique, en Dérivés Hydroxycinnamiques Totaux et Activité Antioxydante Chez les Apiacées, les Borraginacées et les Lamiacées Médicinales", Ann. Pharmaceutiques françaises, 1990, vol. 48, No. 2, pp. 103-108.
World Patent Index, XP-002532462, JP 2000-353406, Jun. 25, 2009.
Zouboulis, C.C., et al. "Acne and Sebaceous Gland Function", Dermatology (2004) vol. 22, pp. 360-366.
Tamarkin, D., "TU-2100—A Novel Topical Sebostatic Preparation", iptechex Pharmalicensing, http://pharmalicensing.com/public/articles/view/949514185_38986fc914957, May 13, 2008.
Layton, A.M., "Optimal Management of Acne to Prevent Scarring and Psychological Sequelae", Amer. J. Clin. Dermatol. (2001) vol. 2, No. 3, pp. 135-141 (Abstract enclosed).

* cited by examiner

*Primary Examiner* — Amy L Clark
(74) *Attorney, Agent, or Firm* — Drinker Biddle & Reath LLP

(57) ABSTRACT

The present invention relates to a novel sebum secretion inhibitor and use thereof for the production of cosmetic and pharmaceutical, notably dermatological, compositions, intended for preventing and/or reducing the secretion of sebum and notably of squalene.

12 Claims, No Drawings

SEBUM SECRETION INHIBITORY AGENT

This application claims the priority benefit of French Application No. 0858183, filed Dec. 1, 2008, and U.S. Provisional Application Ser. No. 61/121,917, filed Dec. 12, 2008.

The present invention relates to a novel sebum secretion inhibitor and use thereof for the production of cosmetic and pharmaceutical, notably dermatological, compositions intended to prevent and/or reduce the secretion of sebum and notably of squalene.

Sebum is produced by the sebaceous glands of the skin and is constituted of a mixture of lipids intended notably to protect the skin against drying out, against microbes by acidification, and to preserve its flexibility. Squalene or (E) 2,6,10,15,19,23-hexamethyl-2,6,10,14,18,22-tetracosa-hexaene, generally known by the names Spinacene and Suprene, is one of the lipids that is present in large amounts and is characteristic of human sebum.

Although the secretion of sebum is useful because of these skin protecting functions, it gives the skin, especially when it is excessive, an appearance which is often described as shiny, dull, or greasy, and sometimes causes dilatation of the pores and/or the formation of blackheads, manifestations that are often perceived as unaesthetic and/or unpleasant and/or uncomfortable.

Moreover, this seborrhoea can be the cause of real pathologies such as seborrhoeic eczema, and/or hypersecretion in nursing infants (commonly known as "milk crust").

Numerous actives are available in the fields of cosmetics and dermatology for preventing and/or reducing the secretion of sebum directly. These agents, called seboregulators, directly reduce the production of sebum by the sebaceous glands, for example zinc gluconate and azelaic acid. Other agents are also used for their indirect action on the secretion of sebum, in particular exfoliating agents, stimulators of cell renewal, agents with astringent and/or matifying action by absorption of sebum.

At present, however, the applicant knows of no active that is capable of providing, in a satisfactory manner, an effect on the secretion of sebum that is at the same time visible, rapid and durable, without causing a rebound effect, or irritation of the skin and without loss of its radiance. It is the intention of the present invention to identify a novel inhibitor of the secretion of sebum, in particular of squalene, for use as an alternative to the actives available on the market. Identifying a sebum secretion inhibitor that in addition is able to prevent and/or reduce the secretion of sebum in a visible, rapid and long-lasting manner, and advantageously without causing a rebound effect and/or without irritating the skin and/or without a loss of its radiance notably by complexing with the sebum is thus of considerable interest cosmetically and/or pharmaceutically, notably dermatologically.

According to the present invention, it was discovered particularly surprisingly and unexpectedly that the *Orthosiphon stamineus* extract can solve all of these technical problems. It has in fact been discovered that the *Orthosiphon stamineus* extract can prevent and/or reduce the secretion of sebum and notably of squalene very effectively.

*Orthosiphon stamineus* is a plant belonging to the genus *Orthosiphon*, in the Lamiaceae family. It is commonly called "Java Tea". Extracts of this plant have already been described in cosmetic applications for a whitening, antioxidant or antimicrobial effect (JP2000095663). Moreover, in general, plants belonging to the genus *Orthosiphon* have also been described in the treatment of prostatic hypertrophy (WO2005087245).

None of the known properties of this extract, however, suggested its effect for preventing and/or limiting the secretion of sebum, and in particular of squalene as discovered in the present invention.

The *Orthosiphon stamineus* extract notably has the advantage that it is not irritant, it does not complex with sebum, and it is effective very quickly, quite especially on skin of the Caucasian and/or Asian type. Moreover, apart from its action in preventing and/or reducing the secretion of sebum, *Orthosiphon stamineus* extract has the advantage of preserving and/or of improving the radiance of the complexion. This is due notably to the fact that it does not complex with the sebum, does not scour the skin and in particular does not attack it, like some agents of the prior art.

The extract acts instead on regulating the secretion of sebum by the sebaceous gland directly and with a lasting, long-term effect. This has the advantage that the natural radiance of the complexion is preserved. Moreover, the *Orthosiphon stamineus* extract improves the radiance of the complexion by preventing and/or reducing skin imperfections linked to a high level of sebum production. It has notably been observed that the extract according to the invention refines the grain of the skin by reducing the pore size and making it more even.

Some of these properties of the *Orthosiphon stamineus* extract according to the invention will notably be demonstrated in more detail in the examples supplied below concerning the secretion of sebum, and in particular of squalene.

The present invention thus relates to the cosmetic use of an *Orthosiphon stamineus* extract for preventing and/or reducing and/or delaying the secretion of sebum, in particular of squalene and for preventing and/or reducing the unaesthetic and/or unpleasant and/or uncomfortable manifestations associated with the secretion of sebum, notably for preventing and/or reducing and/or delaying the dilatation of the pore size of the skin and/or the formation of blackheads and/or the shiny appearance of the skin and/or of the hair and/or comedogenesis.

The present invention also relates to the use of an *Orthosiphon stamineus* extract for preparing a pharmaceutical, notably dermatological composition intended to prevent and/or treat at least one pathology associated with hyperproduction of sebum, notably of squalene and in particular pathological hyperseborrhoeas, seborrhoeic eczema and/or hypersecretion in nursing infants and/or any combination thereof.

The present invention also relates to a cosmetic or pharmaceutical, notably dermatological composition comprising an *Orthosiphon stamineus* extract in combination with at least one agent selected from seboregulating agents, preferably selected from sarcosine, zinc salicylate, zinc gluconate, azelaic acid and/or their derivatives, and/or at least one agent with a complementary property selected from exfoliating agents, keratolytic agents, agents stimulating the synthesis of fibronectin, agents for protecting fibroblast growth factor (FGF2), agents stimulating the growth of fibroblasts, an antibacterial agent, a sebum absorber, a comedolytic agent, a local antibiotic and any mixture thereof. In a particular embodiment, the *Orthosiphon stamineus* extract is contained in this cosmetic or pharmaceutical composition at a concentration between 0.001 and 10% by weight, and advantageously between 0.01 and 5% by weight of the total composition and preferably between 0.1 and 3% by weight of the total composition.

The present invention also relates to the use of such a cosmetic composition for preventing and/or reducing and/or delaying the secretion of sebum, in particular of squalene and/or for preventing and/or reducing and/or delaying the dilatation of the pore size of the skin and/or the formation of blackheads and/or the shiny appearance of the skin and/or of the hair and/or comedogenesis.

The present invention further relates to the use of such a pharmaceutical composition for preventing and/or treating pathologies associated with hyperproduction of sebum, notably of squalene, and especially pathological hyperseborrhoeas, seborrhoeic eczema and/or hypersecretion in nursing infants.

The present invention finally relates to a method of cosmetic care and/or treatment comprising the daily topical application of an *Orthosiphon stamineus* extract according to the invention or of a cosmetic composition according to the invention for preventing and/or reducing and/or delaying the secretion of sebum, in particular of squalene and/or for preventing and/or reducing the unaesthetic and/or unpleasant and/or uncomfortable manifestations associated with the secretion of sebum, notably for preventing and/or reducing and/or delaying the dilatation of the pore size of the skin and/or the formation of blackheads and/or the shiny appearance of the skin and/or of the hair and/or comedogenesis.

The present invention relates to the cosmetic use of an *Orthosiphon stamineus* extract for preventing and/or reducing and/or delaying the secretion of sebum, in particular of squalene, preferably in the form of a cosmetic composition.

The present invention also relates to the cosmetic use of an *Orthosiphon stamineus* extract for preventing and/or reducing and/or delaying hyperseborrhoea.

Advantageously, the present invention can also prevent and/or reduce the unaesthetic and/or unpleasant and/or uncomfortable manifestations associated with the secretion of sebum, in particular of squalene, notably:

by preventing and/or reducing and/or delaying the secretion of sebum, in particular of squalene, by preventing and/or reducing and/or delaying the dilatation of the pores of the skin, by preventing and/or reducing and/or delaying the formation of blackheads, by preventing and/or reducing and/or delaying the shiny appearance of the skin and/or of the hair, and/or by preventing and/or reducing and/or delaying comedogenesis.

Advantageously, the present invention also provides for the cosmetic care and/or treatment of skin described as normal, seborrhoeic, greasy, having a greasy tendency and/or mixed, and of hair described as greasy and/or having a greasy tendency.

The present invention further relates to the cosmetic use of an *Orthosiphon stamineus* extract for the manufacture of a pharmaceutical, notably dermatological composition intended for preventing and/or reducing the secretion of sebum, in particular of squalene.

Advantageously, the present invention makes it possible to prevent and/or reduce at least one pathology associated with hyperproduction of sebum, and in particular of squalene, notably the pathological hyperseborrhoeas, seborrhoeic eczema and/or hypersecretion in nursing infants.

"Sebum inhibitor" means an agent that is able to prevent and/or reduce the secretion of sebum by the sebaceous glands and notably the secretion of squalene.

"Dilatation of the pores of the skin" means an increase in the diameter of the pores of the skin.

"Seboregulating agent" means an agent, plant extract or characterized molecule, capable of regulating, and preferably inhibiting the secretion of sebum and notably of squalene by the sebocytes.

The agent according to the invention is an *Orthosiphon stamineus* extract. This plant belongs to the genus *Orthosiphon* and to the Lamiaceae family and is commonly called "Java Tea".

The agent according to the invention can be extracted from the whole plant or from one or more parts of the plant, notably selected from the root, stem, bark, flower, seed, germ and/or leaf and mixtures thereof. The agent according to the invention is preferably extracted from the leaves of *Orthosiphon stamineus*.

The extract can then be obtained by the methods of extraction from plants known in the field of application, for example by maceration of at least one part of the plant preferably between 1 and 10% (w/w) in a solvent or a mixture of solvents, preferably a protic polar solvent, and advantageously in water, an alcohol, a glycol, a polyol, a water/alcohol, water/glycol or water/polyol mixture (such as water mixed with ethanol, glycerol, butylene glycol or other glycols, such as xylitol etc.) from 100/0 to 0/100 (v/v). The extracts obtained are then preferably centrifuged and/or filtered and/or distilled in order to recover the active soluble fraction (raw extract).

The plant extract is preferably dissolved in a solvent, notably a polar solvent, such as water, an alcohol, a polyol, a glycol, or a mixture thereof.

The active substance can be concentrated by evaporation of the solvent, for example by lyophilization or by spraying.

According to an advantageous embodiment, the agent according to the invention is an extract obtained by hot aqueous extraction, preferably of the leaves, preferably by percolation then, optionally after a drying stage. The extract is then solubilized in an aqueous vehicle, preferably water. The extract is then used in accordance with the present invention, optionally after filtration.

According to a preferred embodiment, the agent according to the invention is an extract obtained by aqueous percolation carried out between 30 and 50° C., preferably between 35 and 40° C.

According to the invention, the *Orthosiphon stamineus* plant extract is preferably used alone or in a cosmetic or pharmaceutical composition at a concentration between $1 \cdot 10^{-4}$ and 10% by weight, and advantageously between $1 \cdot 10^{-4}$ and 5% by weight and more particularly between $1 \cdot 10^{-3}$ and 3% by weight of the final composition.

As previously mentioned, the *Orthosiphon stamineus* extract according to the present invention is preferably used in the form of cosmetic or pharmaceutical, and preferably dermatological compositions.

The compositions according to the invention can contain any suitable solvent and/or any suitable vehicle and/or any suitable excipient, optionally in combination with other compounds of interest.

Accordingly, for said compositions, the excipient contains for example at least one compound selected from the group consisting of preservatives, emollients, emulsifiers, surfactants, moisturizers, thickeners, conditioners, matifying agents, stabilizers, antioxidants, texturizing agents, gloss agents, film-forming agents, solubilizers, pigments, dyes, fragrances and sunscreens. These excipients are preferably selected from the group comprising amino acids and derivatives thereof, polyglycerols, esters, polymers and derivatives of cellulose, derivatives of lanolin, phospholipids, lactoferrins, lactoperoxidases, sucrose-based stabilizers, the E vitamins and derivatives thereof, natural and synthetic waxes, vegetable oils, triglycerides, unsaponifiables, phytosterols, plant esters, silicones and derivatives thereof, protein hydrolysates, jojoba oil and derivatives thereof, fat-soluble/water-soluble esters, betaines, amine oxides, plant extracts, saccharose esters, titanium dioxides, glycines, and parabens, and more preferably from the group consisting of butylene glycol, steareth-2, steareth-21, glycol-15 stearyl ether, cetearyl alcohol, phenoxyethanol, methylparaben, ethylparaben, propylparaben, butylparaben, butylene glycol, natural tocopherols, glycerin, dihydroxycetyl sodium phosphate, isopropyl hydroxycetyl ether, glycol stearate, tri-isononanoin, octyl cocoate, polyacrylamide, isoparaffin, laureth-7, a carbomer, propylene glycol, glycerol, bisabolol, a dimethicone, sodium hydroxide, PEG 30-dipolyhydroxystearate, capric/caprylic triglycerides, cetearyl octanoate, dibutyl adipate, grape seed oil, jojoba oil, magnesium sulphate, EDTA, a cyclomethicone, xanthan gum, citric acid, sodium lauryl sulphate, mineral oils and waxes, isostearyl isostearate, propylene glycol dipelargonate, propylene glycol isostearate, PEG 8, beeswax, glycerides of hydrogenated palm kernel, glycerides of hydrogenated palm oil, lanolin oil, sesame oil, cetyl lactate, lanolin alcohol, castor oil, titanium dioxide, lactose, saccharose, low-density polyethylene, an isotonic saline solution.

Advantageously, the aforementioned compositions are formulated in a form selected from the group consisting of an aqueous or oily solution, a cream or an aqueous gel or an oily gel, notably in a pot or in a tube, notably a shower gel, a shampoo; a milk; an emulsion, a microemulsion or a nanoemulsion, notably oil-in-water or water-in-oil or multiple or siliconized; a lotion, notably in a glass or plastic bottle or in a measuring bottle or in an aerosol; an ampoule; a liquid soap; a dermatological bar; an ointment; a mousse; an anhydrous product, which is preferably liquid, pasty or solid, for example in the form of a stick; powders.

The term "topical application", as used here, signifies applying the composition according to the present invention to the surface of the skin and/or the mucosae, notably by direct application or by spraying.

Preferably, the *Orthosiphon stamineus* extract according to the invention, preferably in the form of a cosmetic composition according to the invention, is applied to at least one area of the body where the secretion of sebum is undesirable and/or excessive, in particular to at least one area of the body where it is uncomfortable, unaesthetic and/or unpleasant, and/or to at least one area displaying hyperseborrhoea, said area or areas preferably being a surface of the body selected from the skin of the face, including the forehead, the cheeks and/or the chin, of the neck, of the back, of the thorax, of the hands, and/or of the chest.

The cosmetic compositions according to the invention are in particular intended for the cosmetic care and/or treatment of normal skin, greasy skin, skin said to have a greasy tendency, and/or mixed skin.

Preferably, the *Orthosiphon stamineus* extract according to the invention, preferably in the form of a pharmaceutical composition according to the invention, is applied to at least one area of the body where the secretion of sebum is excessive, induces and/or is associated with at least one pathology, in particular to at least one area of the body displaying pathological hyperseborrhoea, said area or areas preferably being a surface of the body selected from the skin of the face, including the forehead, the cheeks and/or the chin, of the neck, of the back, of the thorax, of the hands, and/or of the chest.

The pharmaceutical compositions according to the invention are in particular intended for the care and/or treatment of pathological hyperseborrhoea, seborrhoeic eczema and/or hypersecretion in nursing infants.

The term "suitable cosmetic or dermatological vehicle", as used here, signifies that the composition or its components are suitable for use in contact with human skin without causing toxicity, incompatibility, instability, an allergic response, or their equivalents.

Numerous cosmetically active ingredients are known by a person skilled in the art for improving the health and/or the physical appearance of the skin. A person skilled in the art is able to formulate cosmetic or dermatological compositions to obtain the best effects. Furthermore, the compounds described in the present invention can have a synergistic effect when they are combined with one another. These combinations are also covered by the present invention. The CTFA Cosmetic Ingredient Handbook, Second Edition (1992) describes various cosmetic and pharmaceutical ingredients currently used in the cosmetic and pharmaceutical industry, which are suitable in particular for topical application. Examples of these classes of ingredients include, without being limited thereto, the following compounds: abrasives, absorbents, compounds for aesthetic purposes such as fragrances, pigments, dyes, essential oils, astringents, etc. (for example: clove oil, menthol, camphor, eucalyptus oil, eugenol, menthyl lactate, witch hazel distillate), anti-acne agents, anti-flocculating agents, antifoaming agents, antimicrobial agents (for example: iodopropyl butylcarbamate), antioxidants, binders, biological additives, buffering agents, swelling agents, chelating agents, additives, biocidal agents, denaturants, thickeners, and vitamins, and derivatives or equivalents thereof, film-forming materials, polymers, opacifiers, pH adjusters, reducing agents, depigmenting or lightening agents (for example: hydroquinone, kojic acid, ascorbic acid, magnesium ascorbyl phosphate, ascorbyl glucosamine), and conditioning agents (for example: humectants).

Particularly advantageously, the *Orthosiphon stamineus* extract according to the invention can be used, optionally in a cosmetic or pharmaceutical, preferably dermatological, composition, preferably those previously described, as the only active agent, notably as the only seboregulating active agent or in combination with one or more other active agents selected from:

1) another cosmetic and/or dermatological seboregulating agent, preferably sarcosine, zinc gluconate, zinc salicylate, azelaic acid and/or their derivatives, and/or mixtures thereof and/or 2) an agent with complementary properties:

an exfoliating and/or keratolytic agent, in particular alpha-hydroxy acids (AHA) notably salicylic acid, optionally in combination with acacia proteins, malic acid, optionally together with almond proteins, glycolic acid; lactic acid and/or their derivatives; and/or mixtures thereof an agent for stimulating the synthesis of fibronectin, in particular a maize extract, such an extract notably being marketed by the applicant under the name Deliner™ an agent for protecting the fibroblast growth factor (FGF2) of the extracellular matrix against its degradation and/or its denaturation, notably an extract of *Hibiscus abelmoschus* such as described in the patent application in the name of the applicant filed under number FR0654316 and/or a fibroblast growth stimulating agent, for example a fermented soya extract containing peptides, known under the name Phytokine™ marketed by the applicant and also described in patent application EP1119344 B1 (Laboratoires Expanscience), and preferably a combination of these two extracts an agent that stimulates the synthesis of laminin, in particular a biotechnologically modified malt extract, such an extract notably being marketed by the applicant under the name Basaline™;

an agent stimulating the expression and/or activity of hyaluronan synthase 2 (HAS2) such as the plant extracts described in patent application FR2 893 252 A1 and in particular an aqueous extract of Galanga (*Alpinia galanga*);

an agent stimulating the synthesis of lysyl oxidase-like (LOXL) such as those described in patent application FR2855968, and in particular a dill extract;

an agent stimulating the synthesis of intracellular ATP, notably an extract of alga *Laminaria digitata;* a sebum absorbing agent, in particular a talc and/or an absorbent polymer an antibacterial agent notably that described in patent application FR2863893, and in particular an extract of Boldo, such an extract notably being marketed by the applicant under the name Betapur™;

an agent with overall anti-ageing action, notably against pigment spots, in particular nicotinamide or vitamin B3;

a comedolytic agent, in particular retinoic acid and one of its derivatives such as isotretinoin, adapalene and/or 13-cis retinoic acid and benzoyl peroxide;

a local antibiotic agent, in particular erythromycin and/or clindamycin phosphate; and any mixture thereof.

The agents with complementary properties are preferably selected from AHA, a maize extract, an extract of *Hibiscus abelmoschus*, a fermented soya extract containing peptides, a biotechnologically modified malt extract, a talc, an absorbent polymer, an extract of Boldo, retinoic acid or a derivative thereof, benzoyl peroxide, erythromycin, clindamycin phosphate and any mixture thereof.

According to the present invention, the combined use of the *Orthosiphon stamineus* extract according to the invention with the sarcosine molecule, preferably synthetic and/or its derivatives, preferably without another seboregulating agent, is particularly advantageous in that it provides a complete, effective and long-lasting seboregulating action on all skin types, in particular skin described as Caucasian and/or Asian. Sarcosine and/or a derivative thereof is then used at a preferred concentration of between $1·10^{-6}$% and 5% by weight of the total composition, preferably between $1·10^{-5}$% and 0.1% by weight of the total composition and more preferably between $1·10^{-4}$% and $5.10^{-2}$% by weight of the total composition.

The present invention also relates to a method of cosmetic care in which the *Orthosiphon stamineus* extract according to the invention is applied to at least one part of the body, preferably a surface selected from the skin of the face, including the forehead, the cheeks, the chin, the external auditory canal, the skin of the neck, of the back, of the thorax, of the hands, and/or of the chest, preferably for preventing and/or reducing the secretion of sebum, in particular of squalene and/or for preventing and/or reducing the unaesthetic, uncomfortable and/or unpleasant effects from the secretion of sebum.

Advantageously, the *Orthosiphon stamineus* extract according to the invention, preferably in the form of a cosmetic composition according to the invention, is used as a regular and preferably daily topical application for at least 10 days, preferably for 13 days, and more preferably for at least 20 days.

Other aims, characteristics and advantages of the invention will become clear to a person skilled in the art on reading the explanatory description, which refers to examples which are given only as illustration and are not intended to limit the scope of the invention in any way.

The examples form an integral part of the present invention and any characteristic appearing to be novel relative to any prior art following from the description taken in its entirety, including the examples, forms an integral part of the invention in its function and in its generality.

Thus, each example is of a general scope.

Furthermore, in the examples, all the percentages are given by weight, unless stated otherwise, temperatures are expressed in degrees Celsius unless stated otherwise, and the pressure is atmospheric pressure, unless stated otherwise.

EXAMPLES

Example 1: Preparation of an *Orthosiphon stamineus* Extract According to the Invention a) An *Orthosiphon stamineus* extract is obtained from the leaves by percolation with water to 5% (w/w), preferably hot percolation, notably at a temperature between 35 and 40° C.

The percolation time is advantageously between 30 min and 24 hours, with stirring, preferably 10 hours.

The solution is ultrafiltered on ceramic filters with different cutoff thresholds and notably at 0.45 µM.

The extract obtained is then dried notably on a support of the maltodextrin type and then solubilized again in water to 1% (w/w)

b) An *Orthosiphon stamineus* extract is obtained by extraction from the leaves. This extract is obtained from leaves ground to 7% (w/w) in ethanol under reflux or in a mixture with water 75%/25%, preferably in water. Maceration is carried out overnight at 4° C. or room temperature or preferably for 2 hours at room temperature. The solution is ultrafiltered on ceramic filters with different cutoff thresholds and notably at 0.45 µM.

The extract obtained is dried and then solubilized again in water to 1% (w/w).

Example 2: Evaluation In Vitro of the Effect of an *Orthosiphon stamineus* Extract According to the Invention on the Secretion of Sebum in Normal Human Skin Principle:

The principle of this evaluation is based on the measurement of the biosynthesis of squalene, a specific tracer of the production of human sebum by the sebocytes, from radio-labelled mevalonic acid.

Experimental Protocol:

The products tested were:

the extract according to the invention was prepared in accordance with Example 1a) tested at final concentrations of from 0.5% to 2% of extract 1a) in water an aqueous solution of zinc gluconate at 1% (10 mg/mL; $2.2×10^{-2}$ mol/L) in water is used as positive control no solution as negative control The following experiment was carried out for each of the products tested:

1) Freshly taken biopsies of human skin (n=3) are incubated in 5 ml of culture medium in the presence or absence of the test products for 24 h.

2) An amount of radioactive products of 2 μCi of mevalonate 4-$^{14}$C is then added to the biopsies and the whole is incubated again for 24 h.
3) Extraction of the culture media and of the surface of the skin is carried out with isopropyl ether, then the skin samples are dried and weighed as dry weight.
4) The extraction products are analysed by thin-layer chromatography and the quantity of metabolites of $^{14}$C-mevalonate (squalene) is evaluated.

Results for the Biosynthesis of Squalene:

The squalene on the surface of the skin in culture is extracted, then deposited on HPTLC (high-performance thin layer chromatography) plates and migrated after addition of 10 μg of a squalene standard by deposition in the presence of heptane as migration solvent. The radioactivity of the squalene is visualized in a conventional manner. Each radioactive spot corresponding to squalene is scraped onto the HPTLC plates and the radioactivity is measured using a scintillation counter. Each count was expressed in grams of dry tissue.

The results shown in Table 1 below are those obtained on the extracts of culture media and are expressed as a percentage relative to the untreated negative control.

TABLE 1

Results from biosynthesis of squalene for 24 h (dpm $^{14}$C/g dry tissue); measurement of the synthesis of squalene on explants of normal human skin by transformation of 4-$^{14}$[C] mevalonate

| Measurement of squalene synthesis | Mean value | Standard deviation |
|---|---|---|
| Negative control | 100 | 2.9 |
| Zinc gluconate 1% | 76.6 | 2.5 |
| Extract according to the invention at 2% | 70.8 | 2.3 |

Conclusions

These results show that the *Orthosiphon stamineus* extract according to the invention inhibits the formation of squalene and therefore of sebum.

Tests carried out specifically on biopsies of abdominal skin, skin from the breast and skin from the face demonstrated that the *Orthosiphon stamineus* extract according to the invention is equally active on the various types of skin.

Example 3: Evaluation In Vivo of the Effect of an *Orthosiphon stamineus* Extract According to the Invention Principle:

The principle of this evaluation is based on the clinical and instrumental analysis of samples of secretions of sebum using Sebutape™ patches according to the conventional method.

Experimental Protocol:

The products tested were:
the extract according to the invention prepared in accordance with Example 1a) is tested at final concentrations of from 0.5% to 2% of extract 1a) diluted in water
an aqueous solution of zinc gluconate at 1% (10 mg/mL; 2.2×10$^{-2}$ mol/L) in water is used as positive control
no solution as negative control The following treatment was carried out for each of the products tested:

Caucasian and Asian volunteers applied a test product once a day, in blind conditions. Clinical and instrumental assessments, by application of Sebutape™ patches, were carried out on D0, D14 and D28 and the contents of these samples of Sebutape™ patches were analysed quantitatively by image analyser (polarimetric imaging). Determination of the squalene taken in the Sebutape™ patches was carried out as follows:

The Sebutape™ patches were treated by extraction with 10 ml of ether. The lipid residues were deposited on an HPTLC silica gel nanoplate on an aluminium support, one lane of which was reserved for receiving a deposit of 10 μg of squalene standard.

The contents of the plates were subjected to migration in heptane.

The squalene spots were then quantified by densitometry using an instrument of the ChromatoScan CS-93 (Shimadzu) type. Reading was based on absorption at 450 nm and the area of the peaks was expressed in arbitrary units in the table of results given below.

Results for Pore Size: (Clinical Assessment)

After 28 days of treatment, it was observed that pore size was significantly reduced by 30% in the Caucasian volunteers who had applied the extract according to Example 1a) at 2% (p<0.001), a result that is higher than the 17.5% improvement observed in the zinc gluconate group (p<0.01).

Results for the Biosynthesis of Squalene: (Analysis of the Sebutape™ Patches)

The results showed that after 28 days of treatment, the content of squalene in the sebum had decreased by 13% in the subjects who had applied the extract according to Example 1a) at 2% (p<0.01). This improvement was similar to that obtained with zinc gluconate (−14%, p<0.01) and significantly greater than that obtained with the placebo (p<0.001), for which a slight increase in sebum content was observed (+6%, NS).

Results for the Secretion of Sebum: (Analysis of the Sebutape™ Patches)

At 28 days of treatment, the number of active sebaceous glands had decreased by 7.4% in the subjects who had applied the extract according to Example 1a) at 2% (measurement of the number of spots present on the patches compared against D0).

Example 4: Evaluation In Vivo of the Rebound Effect after Application of an *Orthosiphon stamineus* Extract According to the Invention The experiment was conducted on Caucasian and Asian volunteers according to the conditions described in Example 3 for 28 days of treatment (last application on D27 in the evening). Assessments carried out on D30 allowed the persistence of the effect of an extract according to the invention on the production of sebum to be evaluated, two days after stopping the treatment.

Results for Shiny Appearance: (Clinical Assessment)

No rebound effect was observed: two days after stopping the treatment, shiny appearance was significantly reduced by 31% with the extract according to Example 1a) at 2% (p<0.001).

Results for Pore Size: (Clinical Assessment)

Two days after stopping the treatment, the decrease in pore size already observed with the extract according to Example 1a) at 2% persisted and was still significant relative to the first day of the study (−16%, p<0.001).

These results demonstrate both the rapidity of action of an extract according to the invention and the absence of a rebound effect.

Results for Skin Texture: (Self-Evaluation)

Moreover, 2 days after stopping the treatment, 71% of the Asian volunteers who had applied the extract according to Example 1a) at 2% declared that there was refinement of their skin grain (p<0.05). In comparison, only 52% of the volunteers in the group of volunteers who had applied the positive control (zinc gluconate) noticed an improvement in this parameter.

Results for the Secretion of Sebum: (Analysis of the Sebutape™ Patches)

Two days after stopping the treatment, the number of active sebaceous glands had decreased by 14.6% in the subjects who had applied the extract according to Example 1a) at 2%.

The results are summarized below in Table 2:

TABLE 2

| Measurement of the number of spots present on the Sebutape ™ patches after 28 days and 2 days after stopping the treatment, compared against D 0. | | |
|---|---|---|
| Active sebaceous glands, % Dn/D 0 | D 28 | 2 days after D 28 |
| Zinc gluconate 1% | +8.5% | −3.8% |
| Extract according to the invention at 2% | −7.4% | −14.6% |

Example 5: Examples of Preparation of Compositions According to the Invention

Following procedures known by a person skilled in the art, the various parts A, B, C, D, E, or F were mixed together to prepare a composition according to the present invention.

The "products of the invention" represent an *Orthosiphon stamineus* extract preferably obtained according to Example 1a).

The products of the invention can also be in the form of liposomes containing 5% of soya lecithin and incorporating a solution of quaternized soya (600 g final) obtained according to the following embodiment:

30 g of soya lecithin, 12 g of solution of quaternized soya, and 1.5 g of extract of *Orthosiphon stamineus* prepared according to Example 1a) are put in a pill-making machine and diluted in 447 g of laboratory-grade pure water.

After magnetic stirring for 10 minutes at room temperature, the mixture is homogenized vigorously for 10 minutes, thus obtaining a liposomal solution in which the liposomes have an average size which can be between 100 and 800 nanometers depending on the precise conditions of homogenization.

The suspension is then stirred gently for 1 hour. 90 g of butylene glycol, 6 g of phenoxyethanol and 6 g of hydroxyethylcellulose (gelling agent) are then added.

Formulation 5a:

| | | |
|---|---|---|
| A | Water | q.s. 100 |
| | Butylene Glycol | 2 |
| | Glycerol | 3 |
| | Sodium Dihydroxycetyl Phosphate, Isopropyl Hydroxycetyl Ether | 2 |
| B | Glycol Stearate SE | 14 |
| | Triisononanoin | 5 |
| | Octyl Cocoate | 6 |
| C | Butylene Glycol, Methylparaben, Ethylparaben, Propylparaben, pH adjusted to 5.5 | 2 |
| D | Products of the invention | 0.01-10% |

Formulation 5b:

| | | |
|---|---|---|
| A | Water | q.s. 100 |
| | Butylene Glycol | 2 |
| | Glycerol | 3 |
| | Polyacrylamide, Isoparaffin, Laureth-7 | 2.8 |
| B | Butylene Glycol, Methylparaben, Ethylparaben, Propylparaben; | 2 |
| | Phenoxyethanol, Methylparaben, Propylparaben, Butylparaben, Ethylparaben | 2 |
| | Butylene Glycol | 0.5 |
| D | Products of the invention | 0.01-10% |

Formulation 5c:

| | | |
|---|---|---|
| A | Carbomer | 0.50 |
| | Propylene Glycol | 3 |
| | Glycerol | 5 |
| | Water | q.s. 100 |
| B | Octyl Cocoate | 5 |
| | Bisabolol | 0.30 |
| | Dimethicone | 0.30 |
| C | Sodium Hydroxide | 1.60 |
| D | Phenoxyethanol, Methylparaben, Propylparaben, Butylparaben, Ethylparaben | 0.50 |
| E | Perfume | 0.30 |
| F | Products of the invention | 0.01-10% |

What is claimed is:

1. A method of cosmetic care for reducing sebum secretion in an individual in need thereof, comprising:
   a) identifying on the individual an area of skin having a shiny or greasy appearance due to excessive secretion of sebum; and
   b) topically applying onto the area of skin a cosmetic composition comprising an *Orthosiphon stamineus* extract,
   wherein the *Orthosiphon stamineus* extract is in an amount effective to inhibit or reduce formation of squalene in the area of skin.

2. The method of claim 1, wherein the skin is normal skin.

3. The method of claim 1, wherein the area of skin is skin of the face, neck, back, thorax, hands, or chest.

4. The method of claim 1, wherein the *Orthosiphon stamineus* extract is obtained from leaves of *Orthosiphon stamineus* plants.

5. The method of claim 1, wherein the *Orthosiphon stamineus* extract is obtained by hot aqueous extraction.

6. The method of claim 1, wherein the composition contains between about 0.0001% and 10% by weight of the *Orthosiphon stamineus* extract.

7. The method of claim 1, wherein the composition contains between about 0.0001% and 5% by weight of the *Orthosiphon stamineus* extract.

8. The method of claim 1, wherein the composition is topically applied onto the area of skin daily.

9. The method of claim 1, wherein the cosmetic composition further comprises a seboregulating agent selected from the group consisting of sarcosine, zinc salicylate, zinc gluconate, azelaic acid, and mixtures thereof.

10. The method of claim 1, wherein the cosmetic composition further comprises an additional component selected from the group consisting of AHA, a maize extract, an extract of *Hibiscus abelmoschus*, a fermented soya extract containing peptides, a biotechnologically modified malt extract, a talc, an absorbent polymer, an extract of Boldo, retinoic acid, benzoyl peroxide, erythromycin, clindamycin phosphate and mixtures thereof.

11. The method of claim 1, wherein the area of skin being treated has reduced and/or delayed shiny appearance.

12. The method of claim 1, wherein the area of skin being treated has reduced and/or delayed dilatation of pore size.

\* \* \* \* \*